United States Patent [19]

Cleare

[11] 4,018,838

[45] Apr. 19, 1977

[54] PROCESS OF PREPARING ALKENES

[75] Inventor: Peter John Vernon Cleare, Ascot, England

[73] Assignee: Imperial Chemical Industries Limited, London, England

[22] Filed: Apr. 9, 1976

[21] Appl. No.: 675,267

[30] Foreign Application Priority Data

Apr. 17, 1975 United Kingdom ............ 15862/75

[52] U.S. Cl. ...................... 260/654 R; 260/654 D; 260/632 R
[51] Int. Cl.² ........................................ C07C 21/00
[58] Field of Search ............ 260/654 R, 654 D, 655

[56] References Cited

FOREIGN PATENTS OR APPLICATIONS 11,041  6/1967  Japan .............................. 260/654 R

*Primary Examiner*—Delbert E. Gantz
*Assistant Examiner*—Joseph A. Boska
*Attorney, Agent, or Firm*—Cushman, Darby & Cushman

[57] ABSTRACT

The invention relates to the reductive dehydrohalogenation of $\alpha$-haloalcohols to alkenes with powdered zinc in glacial acetic acid.

7 Claims, No Drawings

PROCESS OF PREPARING ALKENES

This invention relates to reductive dehydrohalogenation of α-haloalcohols to give alkenes, and more particularly it relates to the reductive dehydrochlorination of chloral adducts with alkenes.

Farkas et al (Collection Czechoslov. Chem. Commun., (1959), 24 2230-2236) describes the preparation of 1,1-dichloro-4methyl-1,3-pentadiene. This compound is useful as an intermediate in the preparation of insecticidal esters (for example, the allylrethrolonyl ester) of 2(2,2-dichlorovinyl)-3,3-dimethylcyclopropane carboxylic acid which can be obtained by the reaction of the above pentadiene with ethyl diazoacetate followed by hydrolysis of the ethyl ester. The procedure for preparation of the pentadiene described by Farkas et al involves condensation of chloral with isobutylene according to the method of Colonge et al (Bull. soc. chim. France, (1957) 204) to yield a mixture of 1,1,1-trichloro-2-hydroxy-4-methyl-3-pentene and 1,1,1-trichloro-2-hydroxy-4-pentene, followed by preparation of the mixed acetates thereof. Treatment of the mixed acetates with about 4 equivalents of zinc dust in a mixture of diethyl ether and acetic acid yields a mixture of 1,1-dichloro-4-methyl-1,3-pentadiene and 1,1-dichloro-4-methyl-1,4-pentadiene which on heating with a small amount of p-toluenesulphonic acid yields substantialy pure 1,1-dichloro-4-methyl-1,3-pentadiene.

This procedure is not well suited to large scale preparation of the required diene because it involves a large number of separate steps, it uses a relatively large quantity of zinc dust which can give rise to problems of effluent disposal, and uses ether in conjunction with the zinc powder at one stage which makes that particular step potentially very hazardous because of the high flammability and low flash point of ether and the pyrophoric nature of finely powdered zinc dust.

We have now discovered that the above procedure can be improved by reduction of the number of steps involved, by eliminating the need for such a large excess of zinc dust, and by elimination of the need for ether in conjunction with zinc dust. Furthermore the improved procedure may equally well be used for the preparation of other 1,1-dihalo-4-methyl-1,3-pentadienes and 1,1-dihalo-4-methyl-1,4-pentadienes.

According to the present invention an improved process for the preparation of a compound of formula:

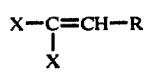

wherein X is halogeno and R is either a group of formula:

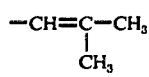

or a group of formula:

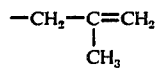

comprises treating a haloalcohol of formula:

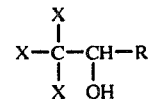

with powdered zinc in glacial acetic acid at a temperature within the range 25° to 110° C, wherein the zinc is used in an amount of from one to two moles per mole of haloalcohol.

The improved process is preferably conducted at a temperature within the range 40° to 60° C. The quantity of zinc used is preferably within the range from 1.4 to 1.6 moles of zinc per mole of haloalcohol. As will be readily appreciated the use of zinc in the amounts specified in the invention process represents a considerable saving over the amounts proposed by Farkas et al. This saving is not only made as a result of using less zinc, which is in itself valuable, but also in the reduction of the cost involved in plant and processes to recover the spent zinc from the reaction mixture and also a reduction in the cost of providing adequate effluent control to prevent wastes contaminated with zinc or zinc salts from affecting the environment.

The improved process of the invention also represents an advance over the known process in that the haloalcohol itself may be directly reduced without the necessity of first converting it to the acetate.

Now the improved process is, as stated above, applicable to the preparation of 1,1-dihalo-4-methyl-1,3-pentadienes and 1,1-dihalo-4-methyl-1,4-pentadienes. These materials may be useful as monomeric intermediates in the preparation of copolymers with other ethylenically unsaturated monomers, for example, vinyl chloride, vinyl acetate, acrylonitrile, methyl methacrylate, and the like. They may also be useful in the preparation of resins, for example, alkyd resins. By the term "halo" or "halogeno" as used herein we mean fluoro, chloro, bromo and iodo.

The 1,1-dihalo-4-methyl-1,3-pentadienes are also useful in the synthesis of certain insecticidal cyclopropane derivatives. 1,1-Dichloro-4-methyl-1,3-pentadiene and 1,1-dibromo-4-methyl-1,3-pentadiene are particularly useful for this purpose, and can be reacted with alkyl diazoacetates to provide the alkyl esters of 2(2,2-dichlorovinyl)-3,3-dimethylcyclopropane caraboxylic acid, and 2(2,2-dibromovinyl)-3,3-dimethylcyclopropane carboxylic acid respectively. Certain esters of these acids, for example, the 3-phenoxybenzyl, and α-cyano-3-phenoxybenzyl esters, are extremely potent insecticides.

Although it is the 1,1-dihalo-4-methyl-1,3-dienes which are directly useful in the synthesis of these insecticidal cyclopropane derivatives, these conjugated dienes may be obtained from the corresponding unconjugated 1,4-dienes, for example by heating with an organic acid.

In a preferred form the invention provides a process for the preparation of a compound of formula:

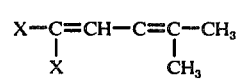

wherein X is chloro or bromo, which comprises (a) the step of treating a haloalcohol of formula:

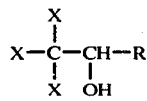

wherein R represents either the group of formula:

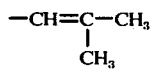

or the group of formula:

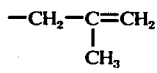

with powdered zinc in glacial acetic acid at a temperature within the range 25° to 110° C, wherein the zinc is used in an amount of from one to two moles per mole of haloalcohol; and (b) the additional step of subsequently heating the reaction mixture at a temperature within the range 80° to 120° C with a catalytic quantity of an organic acid (other than acetic acid), to cause isomerisation of any of the unconjugated 1,4-diene formed in the first stage to the conjugated 1,3-diene. It is particularly convenient to raise the temperature of the reaction mixture for this additional step to the reflux point. p-Toluene sulphonic acid is a preferred organic acid.

The haloalcohols of formula:

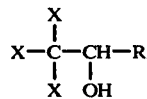

wherein X and R are as defined hereinable, may be obtained by a procedure analogous to that of Colonge et al (loc. cit.), from trihaloacetaldehyde and isobutylene in the presence of a Friedel-Crafts catalyst, for example aluminium chloride. Thus the reaction of anhydrous chloral with isobutylene in this way yields a mixture of 1,1,1-trichloro-2-hydroxy-4-methyl-3-pentene and 1,1,1-trichloro-2-hydroxy-4-methyl-4-pentene. Similarly when anhydrous bromal is reacted with isobutylene a mixture of 1,1,1-tribromo-2-hydroxy-4-methyl-3-pentene and 1,1,1-tribromo-2-hydroxy-4-methyl-4-pentene is formed. These mixtures of isomeric haloalcohols may be used directly in the improved process of the invention or they may be subjected to distillation in order to separate the constituent isomers which may then be used individually in the process of the invention.

The invention is illustrated by the following example.

EXAMPLE 1

This example illustrates the condensation of chloral and isobutylene.

A mixture of anhydrous chloral (738 g), isobutylene (309 g), and petroleum ether (boiling range 40° to 60° C, 800 ml) was stirred at a temperature in the range −5° to −8° C whilst aluminium chloride (54.5 g) was added in small portions over a period of 2 hours. The mixture was stirred for a further period of one hour at 0° C. Water (450 ml) was then added over 15 minutes, the temperature being maintained at 0° C, after which the mixture was allowed to attain to the ambient temperature. The organic phase was separated, washed with brine (3 × 250 ml) and dried over anhydrous magnesium sulphate. After removal of the solvent by evaporation under reduced pressure the residual oil was distilled under reduced pressure and the fraction boiling range 101° to 111° C at 16 to 18 mm Hg pressure collected. This was shown by gas liquid chromatographic examination to consist of approximately 90%, 1,1,1-trichloro-2-hydroxy-4-methyl-4-pentene and approximately 10% 1,1,1-trichloro-2-hydroxy-4-methyl-3-pentene. Careful distillation afforded almost pure (by g.l.c.) 1,1,1-trichloro-2-hydroxy-4-methyl-4-pentene as a colourless oil (boiling point 99°–100° C/16 mm Hg).

EXAMPLE 2

This example illustrates the preparation of 1,1-dichloro-4-methyl-1,3-pentadiene. A stirred mixture of 1,1,1-trichloro-2-hydroxy-4-methyl-4-pentene (671 g) and glacial acetic acid (792 g) was heated to 50° C and powdered zinc (324 g) was added in small portions over a period of 100 minutes, the temperature of the mixture during the addition being maintained in the range 47° to 50° C. When the addition was complete the mixture was stirred at 50° C for a further 4.5 hours. p-Toluenesulphonic acid (4.0 g) was then added to the mixture at the temperature raised 108° C, whilst purging the mixture with nitrogen. The mixture was then heated under a nitrogen atomsphere within the range 105° to 108° C for 8.5 hours, following which acetic acid (ca. 160 ml) was removed from the mixture by distillation, and the residual mixture cooled to the ambient temperature, and diluted with water (900 ml) and light petroleum (boiling range 60° to 80° C, 250 ml). After vigorous stirring the phases were separated. The aqueous phase was washed with more light petroleum (3 × 250 ml) and the washings combined with the original petroleum phase. The combined petroleum phase was washed with saturated aqueous sodium bicarbonate solution (2 × 250 ml), and with water (1 × 250 ml), and finally dried over anhydrous magnesium sulphate. The solvent was removed by evaporation under reduced pressure and the residual oil distilled yielding 1,1-dichloro-4-methyl-1,3-pentadiene, as a fraction boiling within the range 56°–65° C/10-11 mm Hg. The product was identified by n.m.r. spectroscopy and was shown to be identical with an authentic sample.

EXAMPLE 3

The procedure of Example 2 was followed except that the step of distilling off the acetic acid was omitted. This resulted in a slightly higher yield of the product.

I claim:

1. A process for the preparation of a compound of formula:

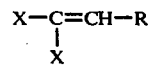

wherein X is halogeno and R is either a group of formula:

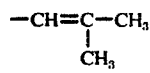

or a group of formula:

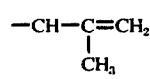

which comprises treating a haloalcohol of formula:

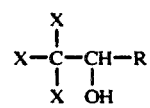

with powdered zinc in glacial acetic acid at a temperature within the range 25° to 110° C, wherein the zinc is used in an amount of from one to two moles per mole of haloalcohol.

2. A process as claimed in claim 1 conducted at a temperature within the range 40° to 60° C.

3. A process as claimed in claim 1 in which the quantity of zinc used is within the range 1.4 to 1.6 moles of zinc per mole of haloalcohol.

4. A process for the preparation of a compound of formula:

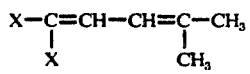

where X is chloro or bromo, which comprises
 a. the step of treating a haloalcohol of formula:

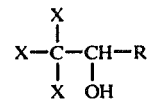

wherein R represents either the group of formula:

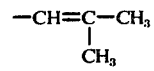

or the group of formula:

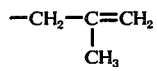

with powdered zinc in glacial acetic acid at a temperature within the range 25° to 110° C, wherein the zinc is used in an amount of from one to two moles per mole of haloalcohol; and
 b. the additional step of subsequently heating the reaction mixture at a temperature within the range 80° to 120° with a catalytic quantity of an organic acid other than acetic acid.

5. A process as claimed in claim 4 wherein the reaction mixture is heated at the reflux temperature in the presence of p-toluenesulphonic acid.

6. A process as claimed in claim 1 in which the haloalcohol is the product obtained by the reaction of a trihaloacetaldehyde and isobutylene in the presence of a Friedel-Crafts catalyst.

7. A process as claimed in claim 4 in which the haloalcohol is the product obtained by the reaction of anhydrous chloral or bromal and isobutylene in the presence of aluminium chloride.

* * * * *